US011014925B2

(12) United States Patent
Li et al.

(10) Patent No.: US 11,014,925 B2
(45) Date of Patent: May 25, 2021

(54) CO-CRYSTALS OF 1-(4-FLUORO-PHENYL)-4-((6BR,1OAS)-3-METHYL-2,3,6B,9,10,10A-HEXAHYDRO-1H,7H-PYRIDO[3',4':4,51_PYRROLO [1,2,3-DELQCUINOXALIN-8-YL)-BUTAN-1-ONE WITH NICOTINAMIDE OR ISONICOTINAMIDE

(71) Applicant: INTRA-CELLULAR THERAPIES, INC., New York, NY (US)

(72) Inventors: Peng Li, New Milford, NJ (US); Edwin Aret, Almere (NL)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 63 days.

(21) Appl. No.: 16/090,152

(22) PCT Filed: Mar. 28, 2017

(86) PCT No.: PCT/US2017/024597
§ 371 (c)(1),
(2) Date: Sep. 28, 2018

(87) PCT Pub. No.: WO2017/172811
PCT Pub. Date: Oct. 5, 2017

(65) Prior Publication Data
US 2019/0112310 A1   Apr. 18, 2019
US 2020/0017500 A9   Jan. 16, 2020

Related U.S. Application Data

(60) Provisional application No. 62/314,339, filed on Mar. 28, 2016.

(51) Int. Cl.
| | | |
|---|---|---|
| C07D 471/16 | (2006.01) | |
| C07D 213/82 | (2006.01) | |
| A61K 31/519 | (2006.01) | |
| C07D 213/81 | (2006.01) | |
| A61K 9/00 | (2006.01) | |
| A61P 25/18 | (2006.01) | |

(52) U.S. Cl.
CPC .......... C07D 471/16 (2013.01); A61K 31/519 (2013.01); C07D 213/81 (2013.01); C07D 213/82 (2013.01); A61K 9/0019 (2013.01); A61K 9/0024 (2013.01); A61P 25/18 (2018.01); C07B 2200/13 (2013.01)

(58) Field of Classification Search
CPC ........................... A61K 9/0019; C07D 471/16
See application file for complete search history.

(56) References Cited

U.S. PATENT DOCUMENTS

| | | |
|---|---|---|
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,115,577 A | 9/1978 | Rajagopalan |
| 4,183,936 A | 1/1980 | Rajagopalan |
| 4,219,550 A | 8/1980 | Rajagopalan |
| 4,238,607 A | 12/1980 | Rajagopalan |
| 4,522,944 A | 6/1985 | Doria et al. |
| 4,971,971 A | 11/1990 | Tokunaga et al. |
| 4,985,432 A | 1/1991 | Tokunaga et al. |
| 5,114,976 A | 5/1992 | Norden |
| 5,151,419 A | 9/1992 | Perenyi et al. |
| 5,576,460 A | 11/1996 | Buchwald et al. |
| 5,648,539 A | 7/1997 | Goodbrand et al. |
| 5,648,542 A | 7/1997 | Goodbrand et al. |
| 5,654,482 A | 8/1997 | Goodbrand et al. |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,847,166 A | 12/1998 | Buchwald et al. |
| 5,902,901 A | 5/1999 | Goodbrand et al. |
| 6,043,370 A | 3/2000 | Kubo et al. |
| 6,166,226 A | 12/2000 | Buchwald et al. |
| 6,235,936 B1 | 5/2001 | Buchwald et al. |
| 6,307,087 B1 | 10/2001 | Buchwald et al. |
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,465,693 B2 | 10/2002 | Buchwald et al. |
| 6,541,639 B2 | 4/2003 | Zhou et al. |
| 6,548,493 B1 | 4/2003 | Robichaud et al. |
| 6,552,017 B1 | 4/2003 | Robichaud et al. |
| 6,699,852 B2 | 3/2004 | Robichaud et al. |
| 6,713,471 B1 | 3/2004 | Robichaud et al. |

(Continued)

FOREIGN PATENT DOCUMENTS

| | | |
|---|---|---|
| EP | 0856508 | 8/1998 |
| EP | 1245553 | 10/2002 |

(Continued)

OTHER PUBLICATIONS

Li, J., et al. "New polymorphs of isonicotinamide and nicotinamide." Chem. Commun. (2011), vol. 47, pp. 1530-1532. (Year: 2011).*
International Search Report for International Application No. PCT/US2018/052922, dated Nov. 26, 2018, 3 pages.
Alvir, J., et al., "Clozapine-Induced Agranulocytosis. Incidence and Risk Factors in the United States," The New England Journal of Medicine, 329(3): 162-167 (1993).
Angst, J., et al., "Prevalence and Characteristics of Undiagnosed Bipolar Disorders in Patients With a Major Depressive Episode," Arch. Gen. Psychiatry, 68(8): 701-709 (2011).

(Continued)

*Primary Examiner* — John S Kenyon
(74) *Attorney, Agent, or Firm* — Hoxie & Associates LLC

(57) ABSTRACT

The disclosure provides new, stable, pharmaceutically acceptable co-crystal forms of 1-(4-fluoro-phenyl)-4-((6bR, 10aS)-3-methyl-2,3,6b,9,10,10a-hexahydro-1H,7H-pyrido [3',4':4,5]pyrrolo[1,2,3-de]quinoxalin-8-yl)-butan-1-one, together with methods of making and using them, and pharmaceutical compositions comprising them.

20 Claims, 6 Drawing Sheets

(56) References Cited

U.S. PATENT DOCUMENTS

| | | | |
|---|---|---|---|
| 6,759,554 | B2 | 7/2004 | Buchwald et al. |
| 6,762,329 | B2 | 7/2004 | Marcoux et al. |
| 6,849,619 | B2 | 2/2005 | Robichaud et al. |
| 6,867,298 | B2 | 3/2005 | Buchwald et al. |
| 6,888,032 | B2 | 5/2005 | Buchwald et al. |
| 6,946,560 | B2 | 9/2005 | Buchwald et al. |
| 7,026,498 | B2 | 4/2006 | Buchwald et al. |
| 7,071,186 | B2 | 7/2006 | Robichaud et al. |
| 7,081,455 | B2 | 7/2006 | Robichaud et al. |
| 7,109,339 | B2 | 9/2006 | Lee et al. |
| 7,115,784 | B2 | 10/2006 | Buchwald et al. |
| 7,183,282 | B2 | 2/2007 | Robichaud et al. |
| 7,223,879 | B2 | 5/2007 | Buchwald et al. |
| RE39,679 | E | 6/2007 | Robichaud et al. |
| RE39,680 | E | 6/2007 | Robichaud et al. |
| 7,238,690 | B2 | 7/2007 | Robichaud et al. |
| 7,247,731 | B2 | 7/2007 | Buchwald et al. |
| 7,323,608 | B2 | 1/2008 | Buchwald et al. |
| 7,375,226 | B2 | 5/2008 | Jolidon et al. |
| 7,462,641 | B2 | 12/2008 | Igo et al. |
| 7,592,454 | B2 | 9/2009 | Lee et al. |
| 7,645,752 | B2 | 1/2010 | McDevitt et al. |
| 7,998,971 | B2 | 8/2011 | Barlow et al. |
| 8,309,722 | B2 | 11/2012 | Tomesch et al. |
| 8,598,119 | B2 | 12/2013 | Mates et al. |
| 8,648,077 | B2 | 2/2014 | Tomesch et al. |
| 8,779,139 | B2 | 7/2014 | Tomesch et al. |
| 8,993,572 | B2 | 3/2015 | Mates et al. |
| 9,168,258 | B2 | 10/2015 | Mates et al. |
| 9,199,995 | B2 * | 12/2015 | Tomesch ............... C07C 309/30 |
| 9,315,504 | B2 | 4/2016 | Tomesch et al. |
| 9,371,324 | B2 | 6/2016 | Mates et al. |
| 9,428,506 | B2 | 8/2016 | Mates et al. |
| 9,616,061 | B2 | 4/2017 | Mates et al. |
| 9,708,322 | B2 | 7/2017 | Li et al. |
| 9,751,883 | B2 | 9/2017 | Tomesch et al. |
| 9,956,227 | B2 | 5/2018 | Vanover et al. |
| 10,117,867 | B2 | 11/2018 | Mates et al. |
| 2001/0008942 | A1 | 7/2001 | Buchwald et al. |
| 2004/0034015 | A1 | 2/2004 | Robichaud et al. |
| 2004/0127482 | A1 | 7/2004 | Robichaud et al. |
| 2004/0186094 | A1 | 9/2004 | Robichaud et al. |
| 2004/0220178 | A1 | 11/2004 | Robichaud et al. |
| 2005/0127482 | A1 | 6/2005 | Fauty et al. |
| 2005/0222209 | A1 | 10/2005 | Zeldis et al. |
| 2005/0239768 | A1 | 10/2005 | Lee et al. |
| 2006/0128713 | A1 | 6/2006 | Jolidon et al. |
| 2006/0148808 | A1 | 7/2006 | Robichaud et al. |
| 2006/0205787 | A1 | 9/2006 | Muller et al. |
| 2007/0066677 | A1 | 3/2007 | Igo et al. |
| 2007/0203120 | A1 | 8/2007 | McDevitt et al. |
| 2014/0050783 | A1 | 2/2014 | Mates et al. |
| 2014/0323491 | A1 | 10/2014 | Tomesch et al. |
| 2014/0364609 | A1 | 12/2014 | Tomesch et al. |
| 2015/0072964 | A1 | 3/2015 | Mates et al. |
| 2015/0079172 | A1 | 3/2015 | Mates et al. |
| 2015/0080404 | A1 | 3/2015 | Mates et al. |
| 2015/0166540 | A1 | 6/2015 | Mates et al. |
| 2016/0031885 | A1 | 2/2016 | Li et al. |
| 2016/0194326 | A1 | 7/2016 | Tomesch et al. |
| 2016/0310502 | A1 | 10/2016 | Vanover et al. |
| 2018/0271862 | A1 * | 9/2018 | Li ..................... A61K 9/0043 |

FOREIGN PATENT DOCUMENTS

| | | |
|---|---|---|
| EP | 1254884 | 11/2002 |
| EP | 1564671 | 8/2005 |
| WO | WO 1998/015515 | 4/1998 |
| WO | WO 1999/043643 | 9/1999 |
| WO | WO 2000/002887 | 1/2000 |
| WO | WO 2000/064899 | 11/2000 |
| WO | WO 2000/077001 | 12/2000 |
| WO | WO 2000/077002 | 12/2000 |
| WO | WO 2000/077010 | 12/2000 |
| WO | WO 2002/085838 | 10/2002 |
| WO | WO 2004/013094 | 2/2004 |
| WO | WO 2004/039788 | 5/2004 |
| WO | WO 2004/056324 | 7/2004 |
| WO | WO 2006/081251 | 8/2006 |
| WO | WO 2007/025103 | 3/2007 |
| WO | WO 2007/084841 | 7/2007 |
| WO | WO 2008/112280 | 9/2008 |
| WO | WO 2009/017836 | 2/2009 |
| WO | WO 2009/100324 | 8/2009 |
| WO | WO 2009/114181 | 9/2009 |
| WO | WO 2009/145900 | 12/2009 |
| WO | WO 2011/133224 | 10/2011 |
| WO | WO 2013/155504 | 10/2013 |
| WO | WO 2013/155506 | 10/2013 |
| WO | WO 2014/145192 | 9/2014 |
| WO | WO 2015/085004 | 6/2015 |

OTHER PUBLICATIONS

Avendaño, C., et al., "The Problem of the Existence of C(Ar)-H . . . N Intramolecular Hydrogen Bonds in a Family of 9-Azaphenyl-9H-carbazoles," J. Chem. Soc. Perkin. Trans., 2: 1547-1555 (1993).

Balbach, S., et al., "Pharmaceutical evaluation of early development candidates 'the 100 mg-approach,'" International Journal of Pharmaceutics, 275: 1-12 (2004).

Bastin, R.J., et al., "Salt Selection and Optimisation Procedures for Pharmaceutical New Chemical Entities," Organic Process Research & Development, 4(5):427-435 (2000).

Beletskaya, I., et al., "Pd- and Cu-catalyzed selective Arylation of Benzotriazole," Tetrahedron Letters, 39: 5617-5620 (1998).

Berger, J., et al., "Synthesis of Some Conformationally Restricted Analogues of Fentanyl," Journal of Medicinal Chemistry, 20(4): 600-602 (1977).

Boger, D., et al., "Inverse Electron Demand Diels-Alder Reactions of Heterocyclic Aza Dienes. Studies on the Total Synthesis of Lavendamycin: Investigative Studies on the Preperation of the CDE β-Carboline Ring System and AB Quinoline-5,8-quinone Ring System," J. Org. Chem., 50:5782-5789 (1985).

Bowman, W.R., et al., "Copper(1) Catalysed Aromatic Nucleophilic Substitution: A Mechanistic and Synthetic Comparison with the SRN1 Reaction," Tetrahedron Letters, 25(50): 5821-5824 (1984).

Bowman, W.R., et al., "Intramolecular Aromatic Substitution (SRN1) Reactions, Use of Entrainment for the Preparation of Benzothiazoles," Tetrahedron Letters, 23(48): 5093-5096 (1982).

Bowman, W.R., et al., "Synthesis of 1H-quinazoline-4-ones using intramolecular aromatic nucleophilic substitution," ARKIVOC, x: 434-442 (2003).

Byrn, S., et al., "Pharmaceutical Solids: A Strategic Approach to Regulatory Considerations," Pharmaceutical Research, 12(7): 945-954 (1995).

Crawford, K., et al., "Copper-catalyzed amidations of bromo substituted furans and thiophenes," Tetrahedron Letters, 43: 7365-7368 (2002).

Davis, R., et al., "ITI-007 demonstrates brain occupancy at sertonin 5-HT2A and dopamine D2 receptors and serotonin transporters using positron emission tomography in healthy volunteers," Psychopharmacology, Published Online Apr. 7, 2015, pp. 1-10.

Davis, R., et al., "ITI-007 in the treatment of schizophrenia: from novel pharmacology to clinical outcomes," Expert Review of Neurotherapeutics, 16(6): 601-614 (2016).

Evindar, G., et al., "Copper- and Palladium-Catalyzed Intramolecular Aryl Guanidinylation: An Efficient Method for the Synthesis of 2-Aminobenzimidazoles," Organic Letters, 5(2): 133-136 (2003).

Ezquerra, J., et al., "Efficient Reagents for the Synthesis of 5-, 7-, and 5,7-Substituted Indoles Starting from Aromatic Amines: Scope and Limitations," J. Org. Chem., 61: 5804-5812 (1996).

Fee, W.W., et al., "Copper (II)-Promoted Solvolyses of Nickel(II) Complexes III. Tetradentate Schiff Base Ligands Containing Various Diamine Segments," Aust. J. Chem., 26: 1475-1485 (1973).

Ferreira, I., et al., "Novel synthetic routes to thienocarbazoles via palladium or copper catalyzed amination or amidation of arylhalides and intramolecular cyclizaiton," Tetrahedron, 58: 7943-7949 (2002).

(56) References Cited

OTHER PUBLICATIONS

Finet, J., et al., "Recent Advances in Ullmann Reaction: Copper(II) Diacetate Catalysed N-, O- and S-Arylation Involving Polycoordinate Heteroatomic Derivatives," Current Organic Chemistry, 6: 597-626 (2002).
Fitzgerald, R., et al., "Inhibition of Caries in Hamsters by 2-Deoxy-D-Glucose," J. Dent. Res., 56(11): 1431 (1977).
Goodbrand, H.B., et al., "Ligand-Accelerated Catalysis of the Ullmann Condensation: Application to Hole Conducting Triarylamines," J. Org. Chem., 64:670-674 (1999).
Grant, "Polymorphism in Pharmaceutical Solids," Chapter 1, 1-10 (1999).
Guillory, "Polymorphism in Pharmaceutical Solids," Chapter 5, 183-226 (1999).
Hackam, D., et al., "Translation of Research Evidence From Animals to Humans," JAMA, 296(14): 1731-1732 (2006).
Hamann, B., et al., "Systematic Variation of Bidentate Ligands Used in Aryl Halide Amination. Unexpected Effects of Steric, Electronic, and Geometric Perturbations," J. Am. Chem. Soc., 120: 3694-3703 (1998).
Hartwig, J.F., "Palladium-Catalyzed Amination of Aryl Halides: Mechanism and Rational Catalyst Design," Synlett, 329-340 (1996).
Hassan, J., et al., "Aryl-aryl bond formation one century after the discovery of the ullmann reaction," Chem. Rev., 102: 1359-1469 (2002).
Haynes, D., et al., "Occurrence of Pharmaceutically Acceptable Anions and Cations in the Cambridge Structural Database," Journal of Pharmaceutical Sciences, 94(10): 2111-2120 (2005).
International Search Report for International Application No. PCT/US2009/003261, dated Jul. 16, 2009, 3 pages.
International Search Report for International Application No. PCT/US2017/024562, dated Jun. 27, 2017, 2 pages.
International Search Report for International Application No. PCT/US2017/024597, dated Jun. 27, 2017, 3 pages.
Ito, T., et al., "Studies of Organic Catalytic Reactions. VI. The Function of Pyridine and Copper in the Rosenmund-von Braun reaction," Bulletin of the Chemical Society of Japan, 41: 419-423 (1968).
Jain, N.K., et al., "Polymorphism in Pharmacy," Indian Drugs, 23(6): 315-316 (1986).
Ji, J. "Selective in of Polyhalpyridines Catalyzed by a Palladium-Xantphos Complex," Organic Letters, 5(24): 4611-4614 (2003).
Jordan, V.C., "Tamoxifen: A Most Unlikely Pioneering Medicine," Nature Reviews: Drug Discovery, 2: 205-213 (2003).
Kametani, T., et al., "A Novel Synthesis of Indole Derivatives," Heterocycles, 14(3): 277-280 (1980).
Kang, S.K., "Copper-catalyzed N-Arylation of Aryl Iodides with Benzamides or Nitrogen Heterocycles in the Presence of Ethylenediamine," Synlett, 3: 427-430 (2002).
Kiyomori A., et al "An Efficient Copper-Catalyzed Coupling of Aryl Halides with Imidazoles," Tetrahedron Letters, 40: 2657-2660 (1999).
Klapars, A., et al., "A General and Efficient Copper Catalyst for the Amidation of Aryl Halides," J. Am. Chem. Soc., 124: 7421-7428 (2002).
Klapars, A., et al., "A General and Efficient Copper Catalyst for the Amidation of Aryl Halides and the N-Arylation of Nitrogen Heterocycles," J. Am. Chem. Soc., 123: 7727-7729 (2001).
Kondratov, S.A., et al., "Nucleophilic Substitution in the Aromatic Series. LV. Reaction of o-Nitrochlorobenzene with Ammonia in the Presence of Copper Compouds," Zhurnal Oranidreskoi Khimii, 51(11): 2387-2390 (1979).
Kwong, F., et al., "Mild and Efficient Copper-Catalyzed Amination of Aryl Bromides with Primary Alkylamines," Organic Letters, 5(6): 793-796 (2003).
Lee, T., et al., "Novel, Highly Potent, Selective 5-HT2A/D2 Receptor Antagonists as Potential Atypical Antipsychotics," Bioorganic & Medicinal Chemistry Letters, 13: 767-770 (2003).
Li, J., et al., "New polymorphs of isonicotinamide and nicotinamide," Chem. Commun., 47: 1530-1532 (2011).
Li, P., et al., "Discovery of a Tetracyclic Quinoxaline Derivative as a Potent and Orally Active Multifunctional Drug Candidate for the Treatment of Neuropsychiatric and Neurological Disorders," Journal of Medicinal Chemistry, 57: 2670-2682 (2014).
Louie, J., et al., "Palladium-Catalyzed Synthesis of Arylamines from Aryl Halides. Mechanistic Studies Lead to Coupling in the Absence of Tin Reagents," Tetrahedron Letters, 36(21): 3609-3612 (1995).
Marcoux, J., et al., "A General Copper-Catalyzed Synthesis of Diaryl Ethers," J. Am. Chem. Soc., 119: 10539-10540 (1997).
Marek, G., et al., "Synergistic Action of 5-HT2A Antagonists and Selective Serotonin Reuptake Inhibitors in Neuropsychiatric Disorders," Neuropsychopharmacology, 28: 402-412 (2003).
Mulrooney, C.A., "Recent Developments in Copper-Catalyzed N-Arylation with Aryl Halides," Essay—University of Pennsylvania.
Murakami, et al., Chem. Pharm. Bull., 43(8): 1281-1286 (1995).
Nagai, Y., et al., "Synthesis of 2,3,4,4a,5,9b-Hexahydro-1H-prido[4,3-b]indole Derivatives and Their Central Nervous System Activities," Journal of Medicinal Chemistry, 22(6): 677-683 (1979).
Newman, A., et al., "Solid-state analysis of the active pharmaceutical ingredient in drug products," Drug Discovery Today, 8(9): 898-903 (2003).
Perlis, R., et al., "Clinical Features of Bipolar Depression Versus Major Depressive Disorder in Large Multicenter Trials," Am. J. Psychiatry, 163: 225-231 (2006).
"Protection for the Amino Group," Protective Groups in Organic Synthesis, Third Edition, John Wiley & Sons, Inc., 494-505 (1999).
Rackova, L., et al., "Free Radical Scavenging and Antioxidant Activities of Substituted Hexahydropyridoindoles. Quantitative Structure—Activity Relationships," J. Med. Chem., 49: 2543-2548 (2006).
Rye, D.B., "Sleep Disorders and Parkinson's Disease," American Parkinson Disease Association, 2000, 2 pages, URL: <http://www.waparkinsons.org/edu_research/articles/Sleep_Disorders.html>.
Sadighi, J., et al "A Highly Active Palladium Catalyst System for the Arylation of Anilines," Tetrahedron Letters, 39: 5327-5330 (1998).
Savjani, K., et al., "Drug Solubility: Importance and Enhancement Techniques," International Scholarly Research Network Pharmaceutics, 2012: 1-10 (2012).
Sigel, H., et al., "Ternary Complexes in Solution. XVI. Influence of the Size of the Chelate Rings on the Stability of Mixed-Ligand Copper(II) Complexes Containing Aliphatic Ligands," Inorganic Chemistry, 13(2): 462-465 (1974).
Singhal, D., et al., "Drug polymorphism and dosage form design: a practical perspective," Advanced Drug Delivery Reviews, 56: 335-347 (2004).
Skoog, "Principles of Instrumental Analysis, 4th Edition," 577 (1992).
Smith, A.D., et al., "Oxford Dictionary of Biochemistry and Molecular Biology," Oxford University Press, 145 (1997).
Snyder, G., et al., "Functional profile of a novel modulator of serotonin, dopamine, and glutamate neurotransmission," Psychopharmacology, 232: 605-621 (2015).
Sugahara, M., et al., "A Facile Copper-Catalyzed Ullmann Condensation: N-Arylation of Heterocyclic Compounds Containing an —NHCO—Moiety,"Chem. Pharm. Bull., 45(4):719-721 (1997).
Wagaw, S., et al., "A Palldium-Catalyzed Method for the Preparation of Indoles via the Fischer Indole Synthesis," Journal of the American Chemical Society, 121(44): 10251-10263 (1999).
Wolfe, J., et al., "An Improved Catalyst System for Aromatic Carbon-Nitrogen Bond Formation: The Possible Involvement of Bis(Phosphine) Palladium Complexes as Key Intermediates," J. Am. Chem. Soc., 118: 7215-7216 (1996).
Wolfe, J., et al "Intramolecular Palladium-Catalyzed Aryl Amination and Aryl Amidation," Tetrahedron, 52(21): 7525-7546 (1996).
Wolter, M., et al., "Synthesis of N-Aryl Hydrazides by Copper-Catalyzed Coupling of Hydrazides with Aryl Iodides," Organic Letters, 3(23): 3803-3805 (2001).
Yamada, K., et al., "A Mild Copper-mediated Intramolecular Amination of Aryl Halides," Synlett, 2: 231-234 (2002).
Yang, B., et al., "The development of efficient protocols for the palladium-catalyzed cyclization reactions of secondary amides and carbamates," Organic Letters, 1(1): 35-37 (1999).

(56) References Cited

OTHER PUBLICATIONS

Zhang, Z., et al., "Highly efficient copper-catalyzed N-arylation of alkylamines with aryl iodides using phosphoramidite as ligand," Catalysis Communications, 6: 784-787 (2005).
Yadav, et al., "Co-Crystals: A Novel Approach to Modify Physicochemical Properities of Active Pharmaceutical Ingredients," Indian J. Pharm. Sci., 71(4):359-370 (2009).

* cited by examiner

CO-CRYSTALS OF 1-(4-FLUORO-PHENYL)-4-((6BR,10AS)-3-METHYL-2,3,6B,9,10,10A-HEXAHYDRO-1H,7H-PYRIDO[3',4':4,5]_PYRROLO [1,2,3-DELQCUINOXALIN-8-YL)-BUTAN-1-ONE WITH NICOTINAMIDE OR ISONICOTINAMIDE

CROSS-REFERENCE TO RELATED APPLICATIONS

This application is a United States Application under 35 U.S.C. § 371 claiming priority to and the benefit of PCT Application No. PCT/US2017/024597, filed Mar. 28, 2017, which claims priority to and the benefit of U.S. Provisional Application Ser. No. 62/314,339, filed on Mar. 28, 2016, the contents of each of which are hereby incorporated by reference in their entireties.

FIELD

This disclosure relates to certain novel co-crystal forms of a substituted heterocycle fused gamma-carboline together with nicotinamide or isonicotinamide, the manufacture of such co-crystals, pharmaceutical compositions thereof, and use thereof, e.g., in the treatment of diseases or abnormal conditions involving or mediated by the 5-HT$_{2A}$ receptor, serotonin transporter (SERT), and/or dopamine D$_1$/D$_2$ receptor signaling pathways.

BACKGROUND 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (sometimes referred to as 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone, or as ITI-007), has the following structure:

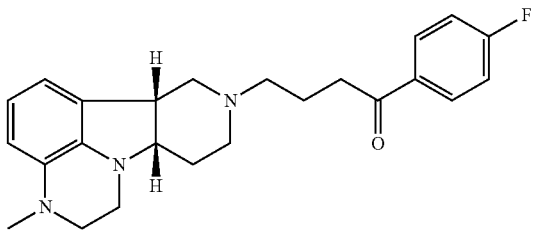 [SMILES: CN1CCN2c3c(cccc31)[C@@H]1CN(CCCC(=O)c3ccc(F)cc3)CC[C@@H]12]

ITI-007 is a potent 5-HT2A receptor ligand (Ki=0.5 nM) with strong affinity for dopamine (DA) D2 receptors (Ki=32 nM) and the serotonin transporter (SERT) (Ki=62 nM) but negligible binding to receptors (e.g., H1 histaminergic, 5-HT2C, and muscarinic) associated with cognitive and metabolic side effects of antipsychotic drugs. ITI-007 is currently in clinical trials, i.e., for treatment of schizophrenia. While ITI-007 is a promising drug, its production and formulation present challenges. In free base form, ITI-007 is an oily, sticky solid, with poor solubility, not only in water but also in many organic solvents. Making salts of the compound has proven to be unusually difficult. A hydrochloride salt form of ITI-007 was disclosed in U.S. Pat. No. 7,183,282, but this salt is hygroscopic and shows poor stability. A toluenesulfonic acid addition salt (tosylate) of ITI-007 was finally identified and described in WO 2009/114181.

There is a need for alternative stable, pharmaceutically acceptable solid forms of ITI-007, which can be readily incorporated into galenic formulations.

SUMMARY

Given the difficulties involved in making salts of ITI-007, it was decided to explore whether the compound was capable of forming co-crystals. An extensive co-crystal screen was undertaken, using 24 potential co-crystal formers and a variety of solvents and crystallization conditions. Two different ITI-007 free base co-crystals were discovered, with nicotinamide and with isonicotinamide. Both co-crystals were obtained by slurry experiments in methanol.

The disclosure thus provides novel co-crystal forms of ITI-007 and nicotinamide and of ITI-007 and isonicotinamide, which co-crystals are especially advantageous for use in the preparation of galenic formulations, together with methods of making and using the same.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
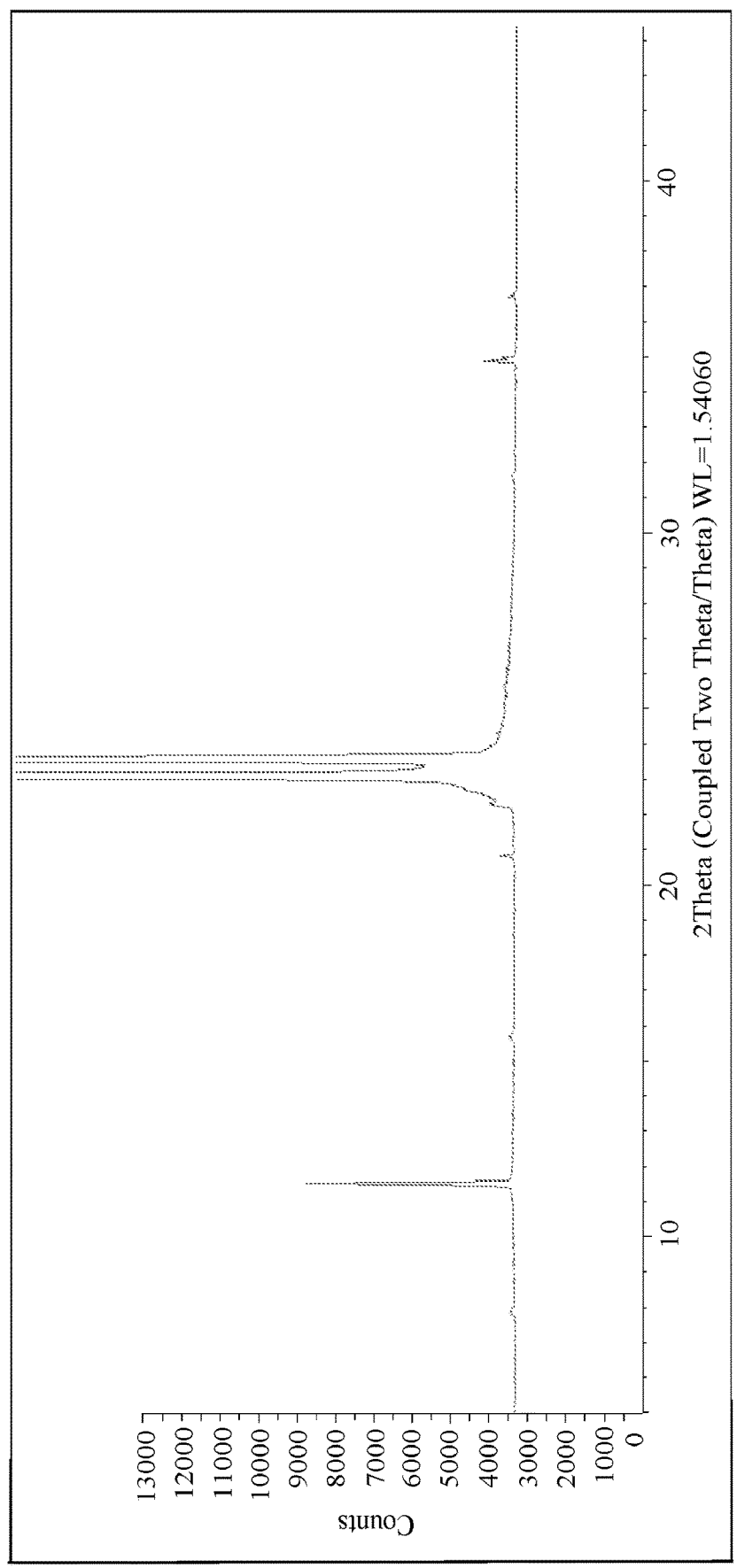
FIG. 1 depicts an X-ray powder diffraction pattern for an ITI-007 free base isonicotinamide co-crystal.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In a first embodiment, the invention provides 1-(4-fluorophenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base in the form of a co-crystal (Co-crystal 1). The invention therefore provides the following:

1.1. Co-crystal 1 wherein the co-crystal is between ITI-007 and a second compound selected from nicotinamide and isonicotinamide.

1.2. Co-crystal 1 or 1.1 in dry crystalline form.

1.3. Co-crystal 1.2 in a homogeneous crystal form, free or substantially free of other forms, e.g., free or substantially free, e.g., less than 10 wt. %, preferably less than about 5 wt. %, more preferably less than about 2 wt. %, still preferably less than about 1 wt. %, still preferably less than about 0.1%, most preferably less than about 0.01 wt. % of amorphous forms.

1.4. Any foregoing Co-crystal when crystallized from a mixture of ITI-007 in free base form and a second compound selected from nicotinamide and isonicotinamide, e.g. in an organic solvent, e.g., comprising methanol or ethanol, which solvent is removed to provide the co-crystal; e.g., wherein the ITI-007 and the second compound are in a molar ratio of about 1:1, and the solvent is methanol or ethanol.

1.5. Co-crystal 1.4, wherein the second compound is nicotinamide, and the Co-crystal is crystallized from methanol.

1.6. Co-crystal 1.4, wherein the second compound is nicotinamide, and the Co-crystal is crystallized from ethanol.

1.7. Co-crystal 1.4, wherein the second compound is isonicotinamide, and the Co-crystal is crystallized from methanol.

1.8. Any foregoing Co-crystal which is an ITI-007 free base-isonicotinamide co-crystal.

1.9. Any foregoing Co-crystal which is an ITI-007 free base-isonicotinamide co-crystal wherein a DSC analysis shows an endothermic event at about 150° C.; e.g. wherein a DSC/TGA analysis shows an endothermic event at $T_{onset}$=136.7° C., $T_{peak}$=149.5° C. and ΔE=−38.1 J/g.

1.10. Any foregoing Co-crystal which is an ITI-007 free base-isonicotinamide co-crystal having an X-ray powder diffraction pattern corresponding to the d-spacing and/or angle (2-theta) values of the following table, for example at least five, or at least six, or at least seven, or at least eight of said values, e.g., taking into account potential variations due to sample purity and instrument variation, for example 2θ shifts due to variation in X-ray wavelength, e.g., wherein the X-ray powder diffraction pattern is generated using an X-ray diffractometer with a copper anode and a nickel filter, e.g., comprising at least those peaks having a relative intensity of at least 0.1, e.g., comprising at least peaks 5 and 6:

| XRPD peak list of the ITI-007 free base-isonicotinamide co-crystal | | | |
|---|---|---|---|
| # | Angle | d Value | Rel. Intensity |
| 1 | 7.894514 | 11.19002 | 0.00066558 |
| 2 | 11.5064 | 7.684276 | 0.03429963 |
| 3 | 15.68352 | 5.645802 | 0.000495557 |
| 4 | 20.83351 | 4.26035 | 0.002273225 |
| 5 | 23.08702 | 3.849343 | 1 |
| 6 | 23.54637 | 3.775279 | 0.1108958 |
| 7 | 25.62448 | 3.473625 | 0.000299336 |
| 8 | 31.55525 | 2.83298 | 0.000438692 |
| 9 | 34.91977 | 2.567342 | 0.001780752 |
| 10 | 36.72755 | 2.445016 | 0.00088104 |

1.11. Any foregoing Co-crystal which is an ITI-007 free base-isonicotinamide co-crystal having an X-ray powder diffraction pattern corresponding to FIG. 1 or FIG. 4, e.g., taking into account potential variations due to sample purity and instrument variation, for example 2θ shifts due to variation in X-ray wavelength, e.g., an X-ray powder diffraction pattern having the peak list shown in Table 1, Table 3 or Table 4, generated using an X-ray diffractometer with a copper anode and a nickel filter.

1.12. Any foregoing Co-crystal which is an ITI-007 free base-isonicotinamide co-crystal having an X-ray powder diffraction pattern having at least 5, or at least 6, or at least 7, or at least 8, peaks having angle (2-theta) values selected from the group consisting of about 7.89, 11.51, 15.68, 20.83, 23.09, 23.55, 25.62, 31.56, 34.92, and 36.73, taking into account potential variations due to sample purity and instrument variation, wherein the X-ray powder diffraction pattern is generated using an X-ray diffractometer with a copper anode and a nickel filter.

1.13. Any foregoing Co-crystal which is an ITI-007 free base-isonicotinamide co-crystal having an X-ray powder diffraction pattern having at least 5, or at least 6, or at least 7, or at least 8, peaks having d-spacing values selected from the group consisting of about 11.19, 7.68, 5.65, 4.26, 3.85, 3.78, 3.48, 2.83, 2.57, and 2.45, taking into account potential variations due to sample purity and instrument variation, wherein the X-ray powder diffraction pattern is generated using an X-ray diffractometer with a copper anode and a nickel filter.

1.14. Any foregoing Co-crystal which is an ITI-007 free base-isonicotinamide co-crystal having an X-ray powder diffraction pattern having at least 5, or at least 6, or at least 7, or at least 8, peaks having angle (2-theta) values and/or d-spacing values as provided in 1.12 and 1.13.

1.15. Any foregoing Co-crystal which is an ITI-007 free base-isonicotinamide co-crystal having an X-ray powder diffraction powder having relative angle (2-theta) values as provided in the table of embodiment 1.10, wherein the values are shifted by up to +/−0.2 degrees, e.g., wherein the values are substantially uniformly shifted by up to +/−0.2 degrees.

1.16. Any foregoing Co-crystal which is an ITI-007 free base-nicotinamide co-crystal.

1.17. Any foregoing Co-crystal which is an ITI-007 free base-nicotinamide co-crystal wherein a DSC analysis shows an endothermic event at about 150° C.

1.18. Any foregoing Co-crystal which is an ITI-007 free base-nicotinamide co-crystal having an X-ray powder diffraction pattern corresponding to the upper pattern in FIG. 2, e.g., taking into account potential variations due to sample purity and instrument variation, for example 2θ shifts due to variation in X-ray wavelength, e.g., an X-ray powder diffraction pattern corresponding to the upper pattern in FIG. 2 generated using an X-ray diffractometer with a copper anode and a nickel filter.

1.19. Any foregoing Co-crystal wherein the ITI-007 is deuterated, e.g., wherein the deuterium:protium ratio at one or more specified positions in the molecule is significantly higher, e.g., at least 2×, for example at least 10× higher, than the natural isotope ratios or the isotope ratios at other positions in the molecule at; for example, any foregoing form of Co-crystal 1 wherein the —CH2- adjacent to the methylated nitrogen moiety and/or adjacent to the carbonyl moiety of ITI-007 is deuterated, e.g., is in the form of —CHD- or —CD2- at levels which are significantly higher than the natural deuterium:protium isotope ratio or the deuterium:protium isotope ratio at other positions in the molecule, and/or wherein the methyl group is deuterated, e.g., is CD3-, e.g., at levels which are significantly higher than the natural deuterium:protium isotope ratio or the deuterium:protium isotope ratio at other positions in the molecule, e.g., as described in WO 2015/154025, the contents of which are incorporated herein by reference.

1.20. Any foregoing form of Co-crystal 1 exhibiting any combination of characteristics as described in 1.1-1.19.

In another embodiment, the invention provides a process (Process 1) for the production of Co-crystal 1, comprising
(a) combining 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base with a second compound selected from nicotinamide and isonicotinamide, e.g., together with an organic solvent, e.g., comprising methanol; e.g., wherein the ITI-007 and the second compound are in a molar ratio of about 1:1, and the solvent is methanol; and
(b) removing the solvent and recovering the Co-crystal thus formed, e.g., recovering a Co-crystal according to any of Co-crystal 1-1.20 above.

In another embodiment, the invention provides a method of purifying 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in free or salt form, comprising combining crude ITI-007 with a second compound selected from nicotinamide and isonicotinamide, in the presence of a solvent, e.g., comprising methanol, removing the solvent and recovering the Co-crystal thus formed, e.g., in accordance with Process 1, and optionally converting the Co-crystal back to ITI-007 free base or to a desired salt form.

In another embodiment, the invention provides the use of a compound selected from nicotinamide and isonicotinamide in a method of isolating and/or purifying ITI-007.

In another embodiment, the invention provides a pharmaceutical composition comprising Co-crystal 1, e.g., any of Co-crystal 1.1-1.20, as active ingredient, in combination or association with a pharmaceutically acceptable diluent or carrier.

In another embodiment, the invention provides a pharmaceutical composition comprising Co-crystal 1, e.g., any of Co-crystal 1.1-1.20, as active ingredient, in combination or association with a pharmaceutically acceptable diluent or carrier, wherein the Co-crystal 1 is predominantly, or is entirely or substantially entirely, in dry crystalline form.

Co-crystal 1, e.g., any of Co-crystal 1.1-1.20, are found to be relatively insoluble. While the free base is poorly soluble, it does not form crystals and is difficult to formulate. Salt forms are quite soluble, but may provide undesirably fast dissolution in extended release formulations. In a particular embodiment, therefore, the invention provides a pharmaceutical composition for extended release of ITI-007, comprising Co-crystal 1, e.g., any of Co-crystal 1.1-1.20, as active ingredient, in combination or association with a pharmaceutically acceptable diluent or carrier, e.g., wherein the pharmaceutical composition is in the form of an injectable depot for extended release.

In another embodiment, the invention provides Co-crystal 1, e.g., any of Co-crystal 1.1-1.20, or a pharmaceutical composition comprising Co-crystal 1, e.g., any of Co-crystal 1.1-1.20, for use in treating a disease or abnormal condition involving or mediated by the 5-HT$_{2A}$ receptor, serotonin transporter (SERT), and/or dopamine D$_1$/D$_2$ receptor signaling pathways, e.g., a disorder selected from obesity, anorexia, bulimia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia.

In another embodiment, the invention provides a method for the prophylaxis or treatment of a human suffering from a disease or abnormal condition involving or mediated by the 5-HT$_{2A}$ receptor, serotonin transporter (SERT), and/or dopamine D$_1$/D$_2$ receptor signaling pathways, e.g., a disorder selected from obesity, anorexia, bulimia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia, comprising administering to a patient in need thereof a therapeutically effective amount of any of Co-crystal 1-1.20.

EXAMPLES

The following equipment and methods are used to isolate and characterize the exemplified co-crystal forms:

X-ray powder diffraction (XRPD): The X-ray powder diffraction studies are performed using a Bruker AXS D2 PHASER in Bragg-Brentano configuration, equipment #1549/#2353. The equipment uses a Cu anode at 30 kV, 10 mA; sample stage standard rotating; monochromatization by a Kβ-filter (0.5% Ni). Slits: fixed divergence slits 1.0 mm (=0.61°), primary axial Soller slit 2.5°, secondary axial Soller slit 2.5°. Detector: Linear detector LYNXEYE with receiving slit 5° detector opening. The standard sample holder (0.1 mm cavity in (510) silicon wafer) has a minimal contribution to the background signal. Measurement conditions: scan range 5-45° 2θ, sample rotation 5 rpm, 0.5 s/step, 0.010°/step, 3.0 mm detector slit; and all measuring conditions are logged in the instrument control file. As system suitability, corundum sample A26-B26-S (NIST standard) is measured daily. The software used for data collection is Diffrac.Commander v2.0.26. Data analysis is done using Diffrac.Eva v1.4. No background correction or smoothing is applied to the patterns.

Simultaneous thermogravimetry (TGA) and differential scanning calorimetry (DSC) or TGA/DSC analysis: The TGA/DSC studies are performed using a Mettler Toledo TGA/DSC1 Stare System, equipment #1547, auto-sampler equipped, using pin-holed Al-crucibles of 40 μl. Measurement conditions: 5 min 30.0° C., 30.0-350.0° C. with 10°

C./min., N2 flow of 40 ml/min. The software used for instrument control and data analysis is STARe v12.10.

Differential scanning calorimetry (DSC): The DSC studies are performed using a Mettler Toledo DSC1 STARe System, equipment #1564. The samples are made using Al crucibles (40 µl; pierced). Typically 1-8 mg of sample is loaded onto a pre-weighed Al crucible and is kept at 30° C. for 5 minutes, after which it is heated at 10° C./min from 30° C. to 350° C. and kept at 350° C. for 1 minute. A nitrogen purge of 40 ml/min is maintained over the sample. As system suitability check Indium and Zinc are used as references. The software used for data collection and evaluation is STARe Software v12.10 build 5937. No corrections are applied to the thermogram.

Polarized light microscopy (PLM): The microscopy studies are performed using an AxioVert 35M, equipped with an AxioCamERc 5s, equipment #1612. The microscope is equipped with four lenses: Zeiss A-Plan 5×/0.12, Zeiss A-Plan 10×/0.25, LD A-Plan 20×/0.30 and Achros TIGMAT 32×/0.40. Data collection and evaluation is performed using Carl Zeiss Zen AxioVision Blue Edition Lite 2011 v1.0.0.0 software. A small amount of sample is loaded on an object glass and carefully spread until a thin layer is obtained.

Dynamic Vapour Sorption (DVS): The Dynamic Vapour Sorption studies are performed using a Surface Measurement Systems Ltd. DVS-1 No Video, equipment #2126. The sample is loaded into a balance pan, typically 20-30 mg, and equilibrated at 0% RH. After the material was dried, the RH is increased with 10% per step for 1 hour per increment, ending at 95% RH. After completion of the sorption cycle, the sample was dried using the same method. The software used for data collection is DVSWin v3.01 No Video. Data analysis is performed using DVS Standard Analysis Suite v6.3.0 (Standard).

Particle size distribution (PSD): The particle size distribution studies are performed using a Malvern Instruments Mastersizer, equipment #1712. The Mastersizer uses a 300RF lens range of 0.05 µm-900 mm. Polydisperse is used as analysis model. Measurement conditions: before each sample measurement a background measurement is performed, the background scan time is 12 seconds (12000 snaps). Each sample is dispersed in Multipar G, refractive index of 1.42. The obscuration range on sample dispersion is between 10%-30%. Each sample is measured 6 times at t=0 and t=30 minutes and the measurement scan time is 10 seconds (10000 snaps). The targeted stirring speed of the sample dispersion unit is 2000±10 rpm. Data collection and evaluation is performed using Mastersizer S Version 2.19 software.

Capillary Melting Point: The capillary melting point is determined on a Büchi Melting Point B-545, equipment #000011, conform USP guidelines.

X-ray fluorescence (XRF): The X-ray fluorescence studies are performed using a Bruker AXS S2 RANGER, equipment #2006. Using an end-window X-ray tube with Palladium anode and an ultra-thin Beryllium window (75 µm) for superior light element analysis. As detector the Xflash V5 detector with Cr, Ti, Al, Ta collimator (energy resolution <129 eV FWHM at 100000 cps Mnkα) is used. The S2 Ranger is equipped with an autosampler with integrated 28 position X-Y automatic sample changer with exchangeable tray, which allows maximum sample diameter of 40 mm. Samples are mounted in steel rings of 51.5 mm diameter for automatic operation. Measurement conditions: disposable liquid cups (35 mm inner diameter, 40 mm outer diameter) with polypropylene foil 5 µm. As system suitability check a copper disk is measured daily and a glass disk, containing several elements, is measured weekly. The software used for data collection is S2 Ranger Control Software V4.1.0. Data analysis is performed using SPECTRA EDX V2.4.3 evaluation software. No background correction or smoothing is applied to the patterns.

Fourier transform infrared spectroscopy (FT-IR): The FT-IR studies are performed using a Thermo Scientific Nicolet iS50, equipment #2357. An attenuated total reflectance (ATR) technique was used with a beam splitter of KBr. Experiment setup of the collected sample is used number of scans 16 with a resolution of 4 from 400 $cm^{-1}$ to 4000 $cm^{-1}$. The software OMNIC version 9.2 is used for data collection and evaluation.

Thermogravimetric analysis (TGA) with infrared spectroscopy (TGA-IR): In TGA-IR, the off-gassing materials are directed through a transfer line to a gas cell, where the infrared light interacts with the gases. The temperature ramp and first derivative weight loss information from the TGA is shown as a Gram-Schmidt (GS) profile; the GS profile essentially shows the total change in the IR signal relative to the initial state. In most cases, the GS and the derivative weight loss will be similar in shape, although the intensity of the two can differ. For this experiment are two devices coupled to each other. The TGA studies are performed using a Mettler Toledo TGA/DSC1 STARe System with a 34-position auto sampler, equipment #1547. The samples are made using Al crucibles (100 µl; pierced). Typically 20-50 mg of sample is loaded into a pre-weighed Al crucible and is kept at 30° C. for 5 minutes after which it is heated at 10° C./min from 30° C. to 350° C. A nitrogen purge of 40 ml/min is maintained over the sample. The TGA-IR module of the Nicolet iS50 is coupled to the TGA/DSC1. The IR studies were performed using a Thermo Scientific Nicolet iS50, equipment #2357. Experiment setup of the collected series, the profile Gram-Schmidt is used number of scans 10 with a resolution of 4. The software OMNIC version 9.2 is used for data collection and evaluation.

High performance liquid chromatography (HPLC): The high performance liquid chromatography analyses are performed on LC-31, equipped with an Agilent 1100 series G1322A degasser equipment #1894, an Agilent 1100 series G1311A quaternary pump equipment #1895, an Agilent 1100 series G1313A ALS equipment #1896, an Agilent 1100 series G1318A column equipment #1897 and an Agilent 1100 series G1314A VWD equipment #1898/LC-34, equipped with an Agilent 1200 series G1379B degasser equipment #2254, an Agilent 1100 series G1311A quaternary pump equipment #2255, Agilent 1100 series G1367A WPALS equipment #1656, an Agilent 1100 series G1316A column equipment #2257 and an Agilent 1100 series G1315B DAD equipment #2258. Data is collected and evaluated using Agilent ChemStation for LC systems Rev. B.04.02[96]. Solutions are prepared as follows: Mobile phase A: Add 800 ml of MilliQ water to a 1 L volumetric flask. Add 1 ml of TFA and homogenize. Fill up to the mark with MilliQ; Mobile phase B: Add 800 ml of Acetonitrile to a 1 L volumetric flask. Add 1 ml of TFA and homogenize. Fill up to the mark with Acetonitrile; Diluent: 50/50 MeOH/ACN.

Example 1

Co-Crystal Screen

Solubility of free base in various solvents is evaluated, and based on the results of the solubility range, suitable solvents are selected for the co-crystal screen. Co-crystal formation is based on hydrogen bonding and stacking of the molecules, meaning the co-former selection is based on active groups. Grinding is a method to form co-crystals, however the free base itself is an oil/sticky solid and therefore not suitable for this method. The free base and counter ion are added to a solution in a certain ratio to give the chance to form a co-crystal, similar to salt formation. We found the best method is to add a saturated solution of the co-former to that of the free base to find an optimal ratio for co-crystal formation.

Three different experiments are performed with each of 26 candidate co-formers, which include sugar alcohols, amino acids, and other compounds identified as having potential to for co-crystals; adding solutions stepwise, slurry experiments and cooling crystallization experiments. The free base and co-former are dissolved prior to adding to each other. Co-formers are added in a 1:1, 2:1 and 1:2 ratio to the free base. All experiments are performed using four different solvents, methanol, acetonitrile, ethyl acetate and toluene. All solids are characterized by XRPD. Two different ITI-007 free base co-crystals formed, with nicotinamide and with isonicotinamide. Both co-crystals were obtained by slurry experiments in methanol.

Example 2

Isonicotinamide Co-Crystal

Isonicotinamide forms a possible co-crystal with ITI-007 free base by slurrying the mixture in methanol and ethyl acetate, appearing as a red/brown and yellow solid respectively. TGA-DSC analysis of the experiment using isonicotinamide in methanol results in two endothermic events, $T_{peak}$=145° C. and $T_{peak}$=185° C. Both endothermic events do not correspond to the free base or the co-former, which means ITI-007 free base-isonicotinamide co-crystal is formed. HPLC and $^1$H-NMR analyses confirm both of the free base and the co-former to be present. Using isonicotinamide in ethyl acetate, however, does not result in a co-crystal and, no endothermic event is present in the TGA/DSC analysis.

The slurry experiment in methanol is repeated at a gram scale. First, ITI-007 free base and isonicotinamide are each dissolved in methanol. Subsequently, the obtained solutions are mixed in a 1:1 ratio and the resulting mixture is stirred at room temperature for 2 hours. The mixture remains a clear solution, which is evaporated under vacuum to give a brown sticky solid. XRPD analysis shows the brown sticky solid to be crystalline, as shown in FIG. 1, ITI-007 free base-isonicotinamide co-crystal has formed. The corresponding peak list is showing in Table 1. The XRPD shows clustered peaks which is likely due to preferred orientation.

TABLE 1

XRPD peak list of ITI-007 free base-isonicotinamide co-crystal (Cu anode, Ni filter)

| # | Angle | d Value | Rel. Intensity |
|---|-------|---------|----------------|
| 1 | 7.894514 | 11.19002 | 0.00066558 |
| 2 | 11.5064 | 7.684276 | 0.03429963 |
| 3 | 15.68352 | 5.645802 | 0.000495557 |
| 4 | 20.83351 | 4.26035 | 0.002273225 |
| 5 | 23.08702 | 3.849343 | 1 |
| 6 | 23.54637 | 3.775279 | 0.1108958 |
| 7 | 25.62448 | 3.473625 | 0.000299336 |
| 8 | 31.55525 | 2.83298 | 0.000438692 |

TABLE 1-continued

XRPD peak list of ITI-007 free base-isonicotinamide co-crystal (Cu anode, Ni filter)

| # | Angle | d Value | Rel. Intensity |
|---|-------|---------|----------------|
| 9 | 34.91977 | 2.567342 | 0.001780752 |
| 10 | 36.72755 | 2.445016 | 0.00088104 |

The free base-isonicotinamide co-crystal is also analyzed by DVS, DSC/TGA and HPLC. The results are summarized in Table 2. DSC/TGA analysis shows one endothermic event at $T_{onset}$=136.7° C., $T_{peak}$=149.5° C. and $\Delta E$=−38.1 J/g. TGA shows three different mass losses, 2.4% in a temperature range of 40° C.-140° C., 12.4% in a temperature range of 150° C.-240° C. and 49.33%, decomposition, in a temperature range of 250° C.-330° C. Analysis of the HPLC data shows both the free base (70 area %) and isonicotinamide (24%) to be present. Analysis of the $^1$H-NMR data shows the free base and isonicotinamide to be present, no shifts are observed, meaning a co-crystal has been formed. FT-IR confirms the chemical structure. Analysis of the DVS data shows a long drying curve for the co-crystal. Only 0.2% mass uptake can be observed at 95 RH %, indicating the co-crystal is not hygroscopic.

TABLE 2

Analytical results scale-up of the FP-212 free base-isonicotinamide co-crystal

| Solvent | Appearance | Hygroscopicity (%) | DSC ($T_{peak}$ ° C.) | Mass loss (%) | HPLC purity (area %) |
|---------|------------|---------------------|------------------------|---------------|----------------------|
| Methanol | Brown sticky solid | 0.2 | 150 | 2<br>12<br>49 | 95* |

*Free base & co-former

Figure 4A:
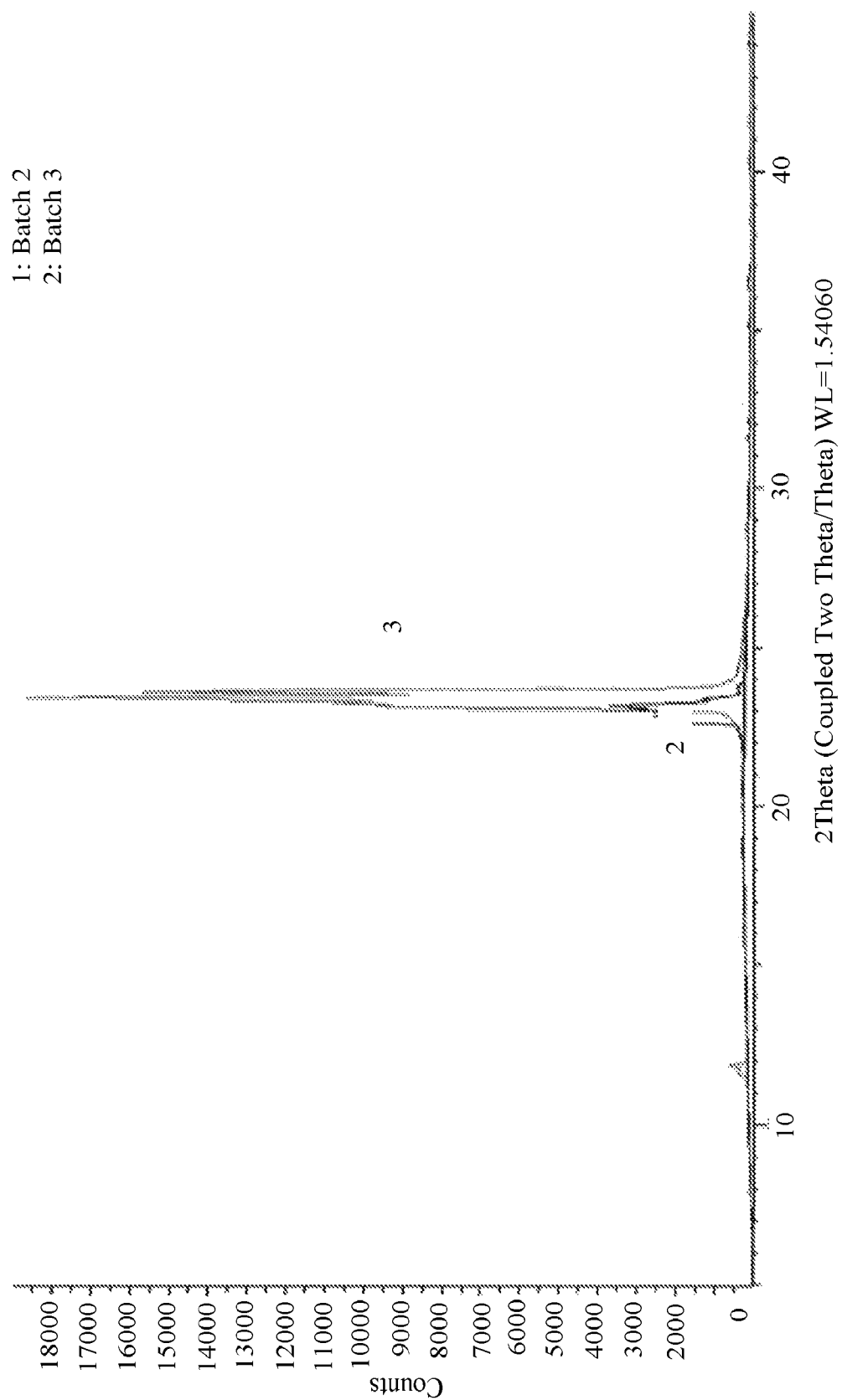
FIGS. 4A and 4B depict over-layed X-ray powder diffraction patterns for scale-up batches of ITI-007 free base isonicotinamide co-crystals.
Figure 4B:
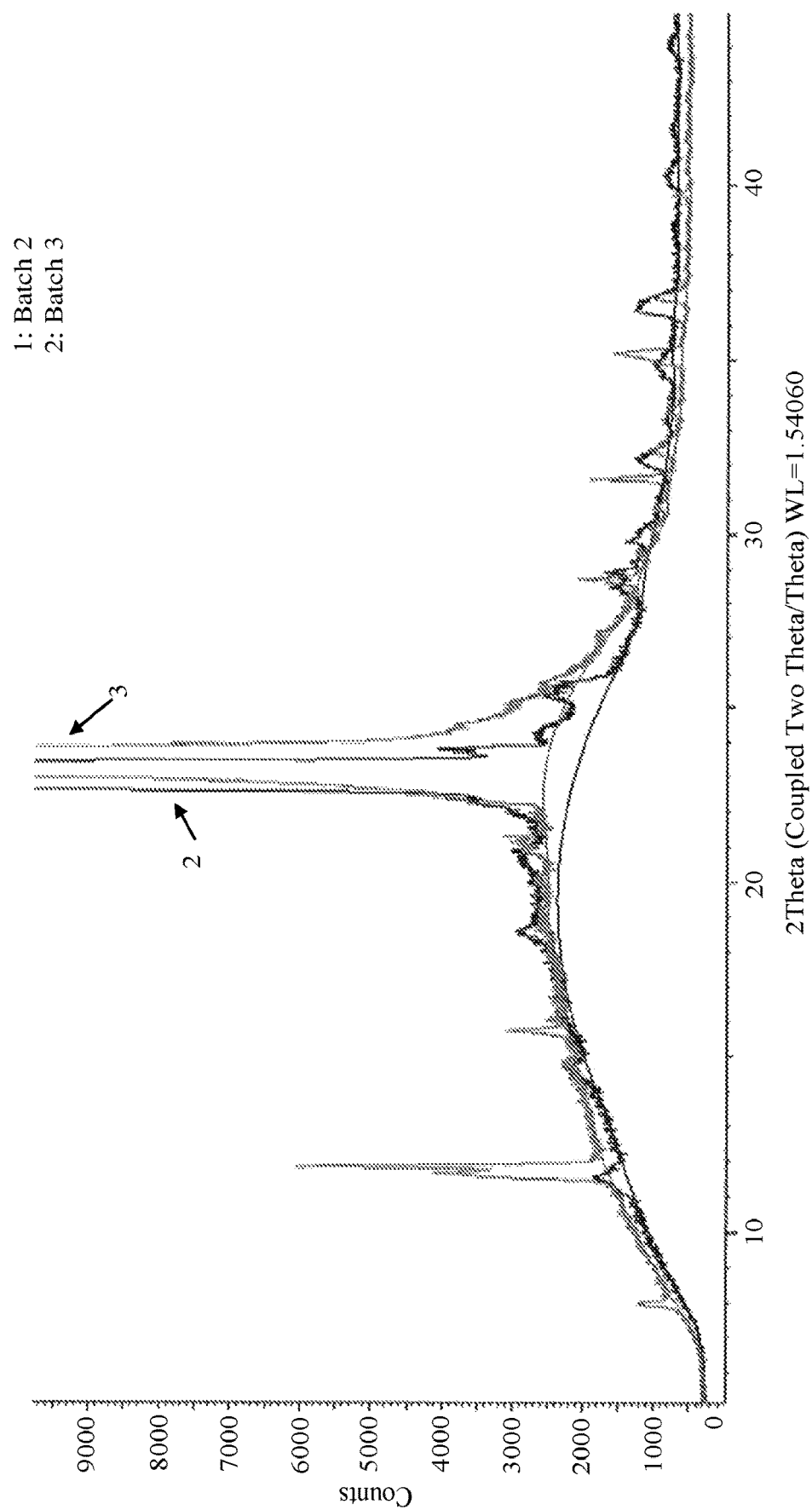

In second and third experiments employing substantially similar conditions for co-crystal formation, each at a 1-gram scale, second batch and third batches of ITI-007 free base-isonicotinamide co-crystal are obtained having the XPRD Peak list shown in Tables 3 and 4, and the XPRD patterns shown in overlay in FIGS. 4A and 4B (zoom-in). The two XRPD images show similar characteristics, but with signals shifted slightly. The total number of counts on the third batch is lower than for the second batch, which suggests that the third batch might be less crystalline. Analytical results for these co-crystals are as shown in Table 5. DSC, TGA and IR are also similar, although the third batch shows slightly higher hygroscopicity. 1H-NMR measurements are substantially the same between the two samples.

TABLE 3

XRPD peak list of ITI-007 free base-isonicotinamide co-crystal (Cu anode, Ni filter)

| # | Angle | d Value | Rel. Intensity |
|---|-------|---------|----------------|
| 1 | 7.963882 | 11.0927 | 0.002458 |
| 2 | 11.65348 | 7.587623 | 0.013524 |
| 3 | 11.78524 | 7.503086 | 0.017218 |
| 4 | 15.72311 | 5.631677 | 0.004795 |
| 5 | 22.50592 | 3.947402 | 0.009079 |
| 6 | 23.22379 | 3.826982 | 0.569613 |
| 7 | 23.37663 | 3.802305 | 1 |
| 8 | 23.53861 | 3.776506 | 0.608281 |
| 9 | 28.64521 | 3.113816 | 0.004175 |

TABLE 3-continued

XRPD peak list of ITI-007 free base-isonicotinamide co-crystal (Cu anode, Ni filter)

| # | Angle | d Value | Rel. Intensity |
|---|---|---|---|
| 10 | 31.57043 | 2.831653 | 0.004148 |
| 11 | 35.14606 | 2.551328 | 0.004628 |
| 12 | 36.78199 | 2.441522 | 0.002748 |

TABLE 4

XRPD peak list of ITI-007 free base-isonicotinamide co-crystal (Cu anode, Ni filter)

| # | Angle | d Value | Rel. Intensity |
|---|---|---|---|
| 1 | 10.01664 | 8.823558 | 0.002930797 |
| 2 | 11.30988 | 7.817352 | 0.009636792 |
| 3 | 11.55688 | 7.650827 | 0.01243575 |
| 4 | 14.6707 | 6.033215 | 0.007486716 |
| 5 | 18.59368 | 4.768201 | 0.01767226 |
| 6 | 20.89626 | 4.247697 | 0.01881626 |
| 7 | 22.01591 | 4.034141 | 0.02451535 |
| 8 | 22.29845 | 3.983659 | 0.03924818 |
| 9 | 22.75855 | 3.904153 | 0.5554008 |
| 10 | 23.01218 | 3.861693 | 0.6624928 |
| 11 | 23.14237 | 3.840262 | 1 |
| 12 | 23.35175 | 3.806301 | 0.2673292 |
| 13 | 23.77056 | 3.740178 | 0.05490891 |
| 14 | 25.32314 | 3.514273 | 0.0251736 |
| 15 | 25.5077 | 3.489263 | 0.01991081 |
| 16 | 25.65148 | 3.47003 | 0.01780625 |
| 17 | 28.32257 | 3.148551 | 0.007050483 |
| 18 | 28.45931 | 3.133733 | 0.01060648 |
| 19 | 28.88088 | 3.088941 | 0.01418584 |
| 20 | 29.81001 | 2.994745 | 0.007920966 |
| 21 | 29.99828 | 2.976378 | 0.006387871 |
| 22 | 31.99688 | 2.794879 | 0.008947632 |
| 23 | 32.12895 | 2.783691 | 0.01130965 |
| 24 | 32.37051 | 2.763468 | 0.007447935 |
| 25 | 36.45062 | 2.462954 | 0.01525544 |
| 26 | 36.66513 | 2.449035 | 0.01064236 |

TABLE 5

Analytical results of second and third scale-ups of the ITI-007 free base-isonicotinamide co-crystal

| Batch | XRPD | Hygro-scopicity (%) | DSC ($T_{peak}$ °C.) | Mass loss (%) (prior melt event) | 1H-NMR Ratio (free base/co-former) | IR (comparison %) |
|---|---|---|---|---|---|---|
| 2 | Clustered peaks | 0.2 | 150 | 2.27 | 1:1 | 84% free base 14% co-former |
| 3 | Clustered peaks | 0.9 | 149 | 1.68 | 1:1 | 86% free base 18% co-former |

Figure 5:
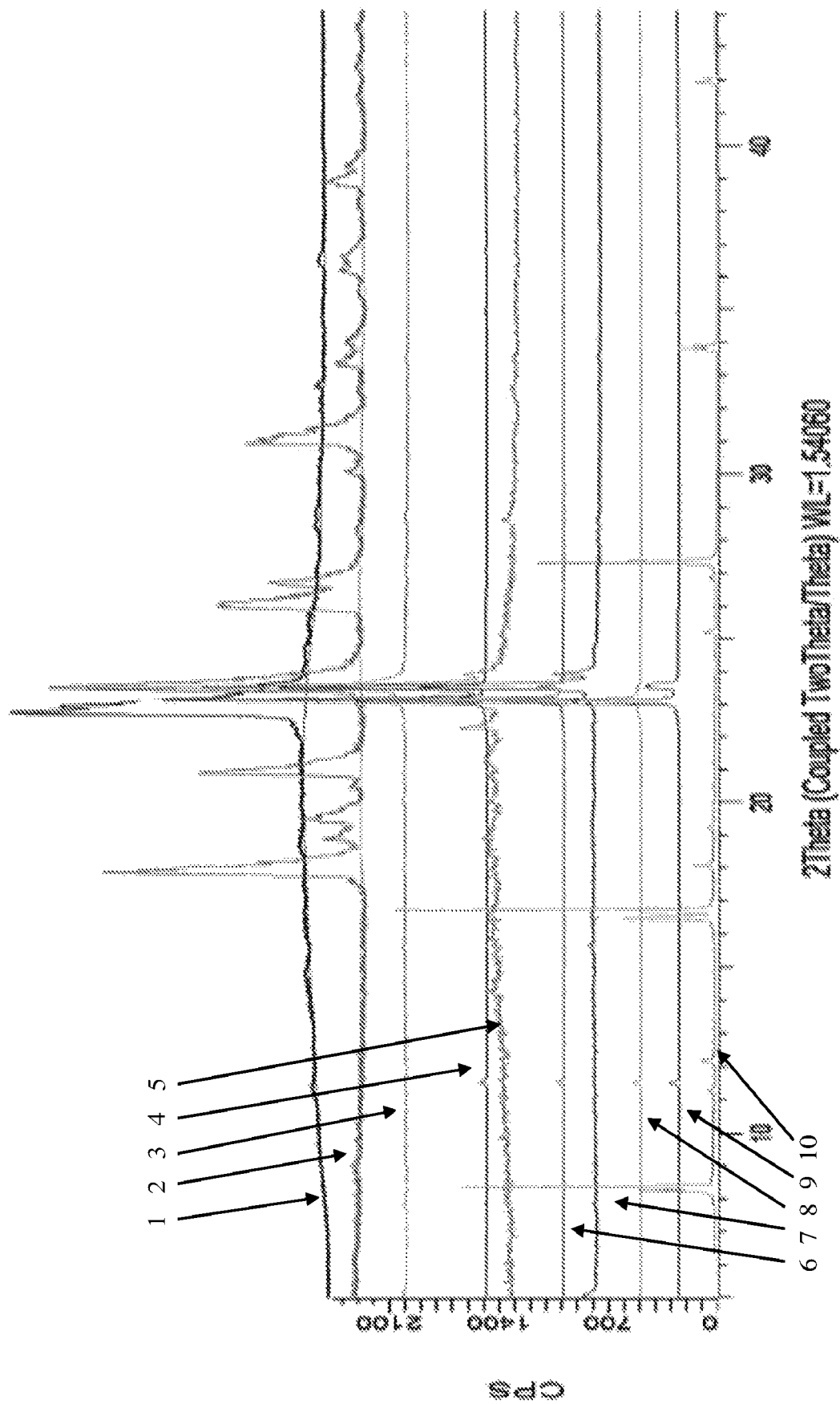
FIG. 5 depicts over-layed X-ray powder diffraction patterns for solids from solubility determination study. Pattern (1) is the third batch co-crystal; pattern (2) is isonicotinamide reference; Patterns (3) to (10) are the solids obtained from solubility studies: (3) dichloromethane, (4) methyl t-butyl ether; (5) acetone; (6) ethyl acetate; (7) ethanol; (8) acetonitrile; (9) toluene; (10) acetic acid (degradation).

Using the third batch of ITI-007 free base-isonicotinamide co-crystal, solubility studies are performed using the shake flask method. About 10 mg of co-crystal is weighed into a vial and solvent is added stepwise. As some solvents are added, crystallization is observed. The use of methanol, acetone or ethanol results in dissolution of the co-crystal to yield a solution. Subsequent evaporation produces solids which are analyzed by XPRD. In contrast, the use of dichloromethane, methyl t-butyl ether, ethyl acetate, acetonitrile or toluene results in the immediate formation of crystals as the solvent is added. Obtained crystals are isolated and are also analyzed by XRPD. XRPD patterns for the material obtained from methanol, dichloromethane, methyl t-butyl ether, acetone, ethyl acetate, ethanol, acetonitrile and toluene all show a common new XPRD pattern with the dominant peak offset from the original co-crystal major peak. These XPRD patterns are shown in overlay in FIG. 5, and they suggest the formation of an additional co-crystal form or a co-crystal polymorph. The use of water or n-heptane in the solubility study results in no interaction with the original co-crystal, while the use of acetic acid results in immediate degradation.

Example 2

Nicotinamide Co-Crystal

Figure 2:
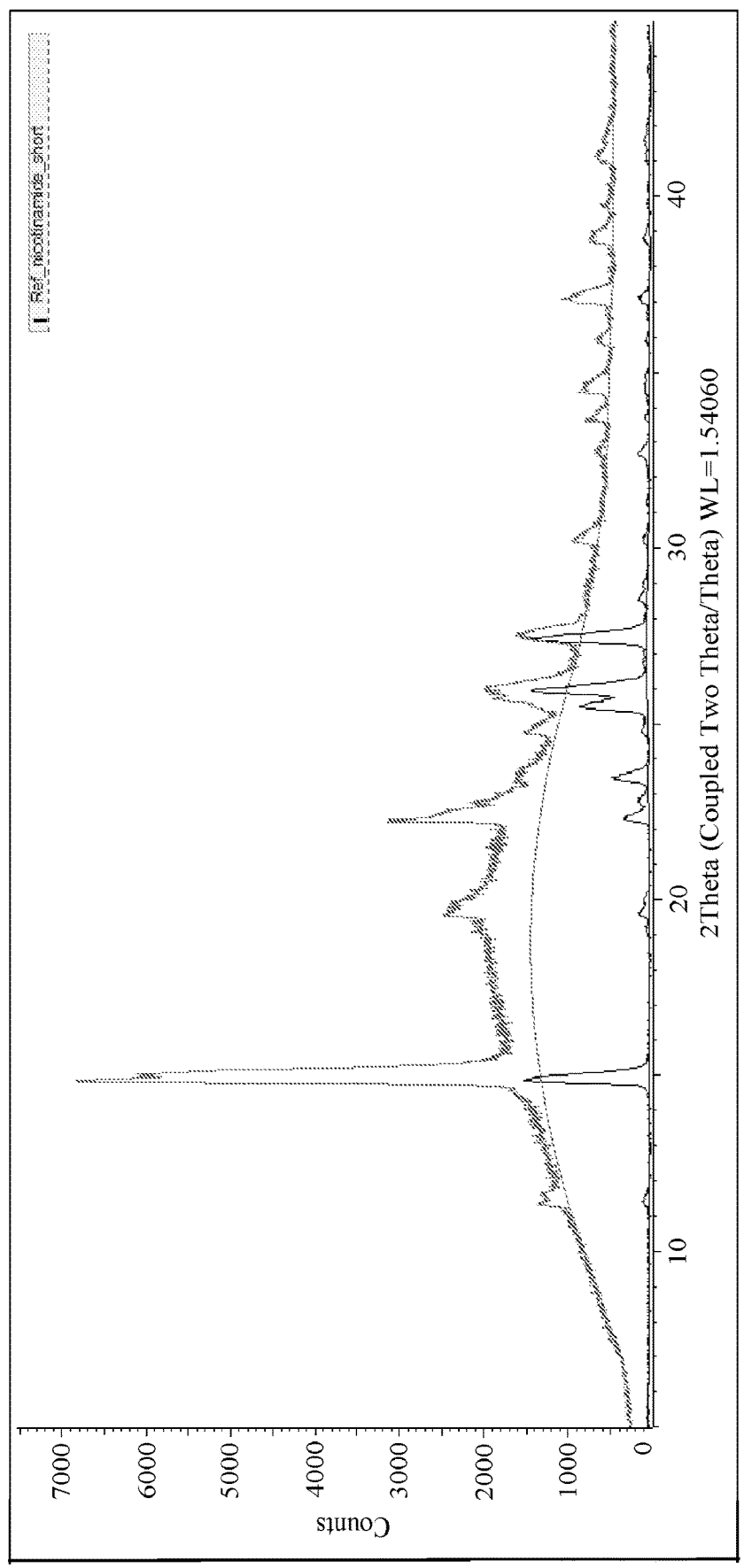
FIG. 2 depicts an X-ray powder diffraction pattern for an ITI-007 free base nicotinamide co-crystal.

For the slurry experiment with nicotinamide in methanol, a solid is formed, for which TGA-DSC shows an endothermic event of $T_{peak}$=120° C. This event is similar to the endothermic event of the free base ($T_{peak}$=120.9° C.), therefore HPLC and $^1$H-NMR analysis are performed. HPLC shows both the free base and the co-former are present, also $^1$H-NMR shows both to be present, meaning a free base-nicotinamide co-crystal is formed. XRPD analysis of the material is depicted in FIG. 2, where the top spectrum is that of the co-crystal, and the bottom spectrum is nicotinamide crystal, to provide a reference.

TGA-DSC analysis of the other slurry experiments using nicotinamide does not show any melting events, meaning the experiments conducted in acetonitrile or ethyl acetate do not form a co-crystal. This experiment is repeated at a gram scale. First, ITI-007 free base and nicotinamide are each dissolved in methanol. Subsequently, the obtained solutions were added in a 1:1 ratio to a vial. The mixture is stirred at room temperature for 2 hours, but no precipitation is observed. The solution is evaporated under vacuum to give a brown sticky solid. XRPD analysis of this brown sticky solid shows this to be nicotinamide itself.

Figure 3:
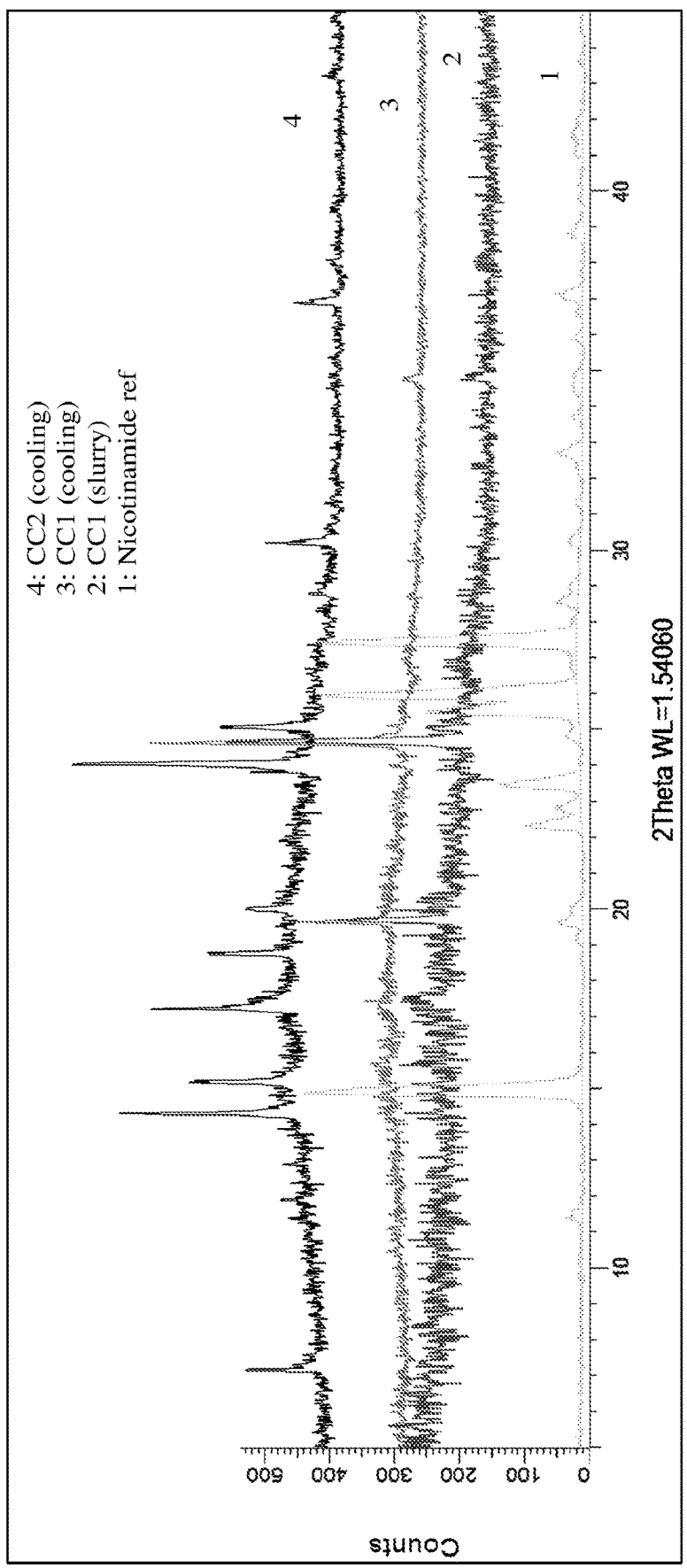
FIG. 3 depicts X-ray powder diffraction patterns for ITI-007 free base nicotinamide co-crystals and nicotinamide reference.

Further experiments are conducted to evaluate other solvent systems for the production and scale-up of the nicotinamide co-crystal. Slurry experiments are performed using a 25 mg of ITI-007 free base and 8.6 mg of nicotinamide co-former in 100 μL of solvent with 24 hours of stirring. The results show that when methanol or ethanol is used, the ITI-007 free base and nicotinamide both dissolve to yield a solution. When attempts are made using isopropanol, 2-butanol, acetonitrile, ethyl acetate, 2-butanone, tetrahydrofuran, or di-isopropyl ether, dissolution does not occur and a white/brown sticky solid is seen to be suspended in the solvent. When water is used, dissolution also does not occur, and a sticky brown solid is seen to be suspended in the water. The solids are filtered and analyzed by XRPD. XRPD analysis for the organic solvents show the presence of nicotinamide, while for the aqueous solution, the solid is amorphous. This shows that of these ten solvents, only methanol or ethanol appear to potentially show the formation of a co-crystal. Evaporation of the methanol and ethanol solutions results in sticky solids. The solid obtained from ethanol evaporation is analyzed by XRPD and shows peaks corresponding to nicotinamide. In contrast, the solid obtained from methanol evaporation is analyzed by XPRD and is consistent with the formation of a co-crystal. XRPD Spectra are shown in FIG. 3 as CC1 (slurry), obtained from methanol. Nicotinamide reference crystal is shown for comparison.

Co-crystals are also attempted using a cooling crystallization method. 25 mg of ITI-007 free base and 8.6 mg of nicotinamide co-former are combined in 200 μL of solvent and heated to 50° C. The mixtures are kept at 50° C. for one hour, then cooled to 5° C. at a rate of 5° C. per hour. The results show that when methanol, ethanol, isopropanol or 2-butanol is used, the ITI-007 free base and nicotinamide both dissolve to yield a solution which remains a solution on cooling. In contrast, the use of acetonitrile, ethyl acetate, 2-butanone, tetrahydrofuran, or di-isopropyl ether does not result in dissolution, and instead, after cooling a white/brown sticky solid is recovered. When water is used, dissolution also does not occur, and a sticky brown solid is recovered. The solids are filtered and analyzed by XRPD. XRPD analysis for the non-alcoholic organic solvents shows the presence of nicotinamide, while for the aqueous solution, the solid is amorphous. This shows that of these ten solvents, only the alcohols appear to potentially show the formation of a co-crystal. Evaporation of the alcoholic solutions results in sticky solids for each. The solids obtained from isopropanol and 2-butanol evaporation are analyzed by XRPD and show peaks corresponding to nicotinamide. In contrast, the solids obtained from methanol and ethanol evaporation are analyzed by XPRD and are shown to be consistent with the formation of a co-crystal. XRPD Spectra are shown in FIG. 3 as CC1 (cooling), obtained from methanol, and CC2 (cooling), obtained from ethanol. Nicotinamide reference crystal is shown for comparison.

The invention claimed is:

1. A co-crystal of 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base and a second compound, wherein the second compound is selected from isonicotinamide and nicotinamide.

2. The co-crystal according to claim 1 which is a co-crystal of ITI-007 free base and isonicotinamide having an X-ray diffraction pattern corresponding to FIG. 1.

3. The co-crystal according to claim 1 which is a co-crystal of ITI-007 free base and nicotinamide having an X-ray diffraction pattern corresponding to the upper pattern on FIG. 2.

4. The co-crystal according to claim 1, wherein the co-crystal is in dry crystalline form.

5. A method making a co-crystal according to claim 1, comprising
    (a) combining 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base with a second compound selected from isonicotinamide and nicotinamide, in an organic solvent, and
    (b) removing the solvent and recovering the co-crystal thus formed.

6. A method of purifying 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in free or salt form, comprising combining crude ITI-007 with a second compound selected from isonicotinamide and nicotinamide, in an organic solvent, removing the solvent and recovering the co-crystal thus formed, and optionally converting the co-crystal back to ITI-007 free base or to a desired salt form.

7. A method for the prophylaxis or treatment of a human suffering from a disease or abnormal condition involving or mediated by the 5-HT$_{2A}$ receptor, serotonin transporter (SERT), and/or dopamine D$_1$/D$_2$ receptor signaling pathways comprising administering to said human an effective amount of a co-crystal according to claim 1.

8. A pharmaceutical composition comprising a co-crystal according to claim 1, in combination or association with a pharmaceutically acceptable diluent or carrier.

9. The pharmaceutical composition of claim 8, wherein the pharmaceutical composition is in the form of an injectable depot for extended release.

10. The co-crystal according to claim 1, wherein the co-crystal is in a homogeneous crystal form, free of other forms.

11. The co-crystal according to claim 10, wherein the co-crystal is in a homogeneous crystal form, free of any amorphous forms of 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one.

12. The co-crystal according to claim 11, wherein the co-crystal comprises less than 2 wt. % of any amorphous forms of 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one.

13. The co-crystal according to claim 1 which is an isonicotinamide co-crystal.

14. The co-crystal according to claim 1 which is a nicotinamide co-crystal.

15. The method according to claim 5 wherein the solvent is methanol, ethanol or a combination thereof.

16. The method according to claim 6, wherein the solvent is methanol, ethanol or a combination thereof.

17. The method according to claim 7, wherein the disease or abnormal condition is a disorder selected from obesity, anorexia, bulimia, depression, anxiety, psychosis, schizophrenia, migraine, obsessive-compulsive disorder, sexual disorders, attention deficit disorder, attention deficit hyperactivity disorder, sleep disorders, conditions associated with cephalic pain, social phobias, or dementia.

18. The method according to claim 17, wherein the disease or abnormal condition is a disorder selected from depression, anxiety, psychosis, schizophrenia, sleep disorders, or dementia.

19. The method according to claim 18, wherein the disease or abnormal condition is a disorder selected from depression and schizophrenia.

20. The co-crystal according to claim 1 which is a co-crystal of ITI-007 free base and isonicotinamide having an X-ray diffraction pattern corresponding to at least six of the d-spacing and/or angle (2-theta) values of the following table:

| #  | Angle    | d Value  |
|----|----------|----------|
| 1  | 7.894514 | 11.19002 |
| 2  | 11.5064  | 7.684276 |
| 3  | 15.68352 | 5.645802 |
| 4  | 20.83351 | 4.26035  |
| 5  | 23.08702 | 3.849343 |
| 6  | 23.54637 | 3.775279 |
| 7  | 25.62448 | 3.473625 |
| 8  | 31.55525 | 2.83298  |
| 9  | 34.91977 | 2.567342 |
| 10 | 36.72755 | 2.445016 | generated using an X-ray diffractometer with a copper anode and a nickel filter.

* * * * *